United States Patent
Springer et al.

(10) Patent No.: US 6,808,883 B1
(45) Date of Patent: Oct. 26, 2004

(54) AUTOMATABLE RAPID TEST FOR DETECTION OF CANCER, BASED ON TELOMERASE (HTC) MRNA WITH SPECIFIC PRIMERS AND PROBES

(75) Inventors: Wolfgang Springer, Wuppertal (DE); Gustav Hagen, Walnut Creek, CA (US); Maresa Wick, Berlin (DE); Dmitry Zubov, Köln (DE)

(73) Assignee: Bayer AG, Leverkusen (DE)

( * ) Notice: Subject to any disclaimer, the term of this patent is extended or adjusted under 35 U.S.C. 154(b) by 0 days.

(21) Appl. No.: 09/959,014
(22) PCT Filed: Apr. 4, 2000
(86) PCT No.: PCT/EP00/02980

§ 371 (c)(1),
(2), (4) Date: Nov. 28, 2001

(87) PCT Pub. No.: WO00/63429
   PCT Pub. Date: Oct. 26, 2000

(30) Foreign Application Priority Data

Apr. 15, 1999 (DE) .......................................... 199 16 929

(51) Int. Cl.[7] .......................... C12Q 1/68; C12P 19/34; C07H 21/04
(52) U.S. Cl. ....................... 435/6; 435/91.2; 536/24.31; 536/24.33
(58) Field of Search .......................... 435/6, 91.2, 810; 536/24.31, 24.33

(56) References Cited

U.S. PATENT DOCUMENTS

| | | | |
|---|---|---|---|
| 5,322,770 A | 6/1994 | Gelfand | 435/6 |
| 5,994,076 A | 11/1999 | Chenchik et al. | 435/6 |
| 6,166,178 A | * 12/2000 | Cech et al. | 530/324 |
| 6,608,188 B1 | * 8/2003 | Tsuchiya et al. | 536/23.5 |

FOREIGN PATENT DOCUMENTS

| | | |
|---|---|---|
| EP | 0 200 362 | 12/1986 |
| EP | 0 320 308 | 6/1989 |
| EP | 0 329 822 | 8/1989 |
| EP | 0420260 | 4/1991 |
| EP | 0 427 074 | 5/1991 |
| GB | 2317891 | 4/1998 |
| WO | WO 87/06270 | 10/1987 |
| WO | 91/14788 | 10/1991 |
| WO | WO 98/14592 | 4/1998 |
| WO | 98/59040 | 12/1998 |
| WO | WO 98/59040 | 12/1998 |
| WO | 99/01560 | 1/1999 |
| WO | 99/35261 | 7/1999 |
| WO | 99/50279 | 10/1999 |
| WO | 00/27858 | 5/2000 |

OTHER PUBLICATIONS

Yu–Sheng Cong, et al, "The human telomerase catalytic subunit hTERT: Organization of the gene and Characterization of the promoter." *Human Molecular Genetics* 8. 137–142, XP–002176111 (1999).

Wick, M., et al, "Genomic organization and promoter characterization of the gene encoding the human telomerase reverse transcriptase (hTERT)." *GENE. (Amsterdam)* 232: 97–106, XP–002176112 (1999).

Zakian, Virginia A.; *Telomeres: Beginning to Understand the End*; Sciencevol. 270; pp. 1601–1607; Dec. 8, 1995.

Meyne, Julianne, et al.; *Conservation of the Human Telomere Sequence (TTAGGG)$_n$ Among Vertebrates*; Proc. Natl. Acad. Sci. USA; vol. 86, pp 7049–7053, Sep. 1989.

McClintock, Barbara; *The Stability of Broken Ends of Chromosomes in Zea Mays*; Genetics 26; pp 234–282; Mar. 1941.

Sandell, Lisa L. and Zakian, Virginia A.; *Loss of a Yeast Telmere: Arrest, Recovery, and Chromosome Loss*; Cell, vol. 75; pp. 729–739; Nov. 19, 1993.

Harley, Calvin B., et al.; *Telomeres Shorten During Ageing of Human Fibroblasts*; Nature, vol. 345; pp. 458–460; May 31, 1990.

Olovnikov, A. M.; *A Theory of Marginotomy: The Incomplete Copying of Template Margin in Enzymic Synthesis of Polynucleotides and Biological Significance of the Phenomenon*; J. Theor. Biol. (1973), vol. 41; pp. 181–190.

Goldstein, Samuel; *Replicative Senescene: The Human Fibroblast Comes of Age*; Science, vol. 249; pp 1129–1133; Sep. 7, 1990.

Allsopp, Richard C., et al.; *Telomere Length Predicts Replicative Capacity of Human Fibroblasts*; Proc. Natl. Acad. Sci. USA; vol. 89; pp. 10114–10118; Nov. 1992.

Hastie, Nicholas D., et al.; *Telomere Reduction in Human Colorectal Carcinoma and With Ageing*; Nature; vol. 346; pp. 866–868; Aug. 30, 1990.

Kim, Nam W., et al.; *Specific Association of Human Telomerase Activity with Immortal Cells and Cancer*; Science, vol. 266; pp. 2011–2015; Dec. 23, 1994.

Broccoli, Dominique, et al.; *Telomerase Activity in Normal and Malignant Hematopoietic Cells*; Proc. Natl. Acad. Sci. USA; vol. 92; pp. 9082–9086; Sep. 1995.

Hiyama, Keiko, et al.; *Activation of Telomerase in Human Lymphocytes and Hematopoietic Progenitor Cells*; Journal of Immunology; vol. 155; pp. 3711–3715; 1995.

Vaziri, Homayoun, et al.; *Evidence for a Mitotic Clock in Human Hematopoietic Stem Cells; Loss of Telomeric DNA with Age*; Proc. Natl. Acad. Sci. USA; vol. 91, pp. 9857–9860; Oct. 1994.

(List continued on next page.)

Primary Examiner—Kenneth R. Horlick
(74) Attorney, Agent, or Firm—Connolly Bove Lodge and Hutz LLP

(57) ABSTRACT

The invention relates to an automatable rapid test for detection of cancer based on telomerase(hTC) mRNA, to suitable starter nucleotides and oligonucleotide probes for this test and to a corresponding detection method and a test kit.

10 Claims, No Drawings

OTHER PUBLICATIONS

Shay, Jerry W., et al.; *Telomerase Assays in the Diagnosis and Prognosis of Cancer*; Telomeres and Telemerase (Ciba Foundation Symposium 211); pp. 148–155 (1997).

Counter, Christopher M., et al.; *Telomere Shortening Associated with Chromosome Instability is Arrested in Immortal Cells Which Express Telomerase Acitivity*; The EMBO Journal; vol. 11, No. 5, pp. 1921–1929; 1992.

Blasco, Maria A., et al.; *Differential Regulation of Telomerase Activity and Telomerase RNA During Multi–Stage Tumorigenesis*; Nature Genetics, vol. 12; pp. 200–204; Feb. 1996.

Dattagupta, Nanibhushan, et al.; *Rapid Identification of Microorganisms by Nucleic Acid Hybridization After Labeling the Test Sample*; Analytical Biochemistry, vol. 177; pp. 85–89; 1989.

Rigby, Peter W. J., et al.; *Labeling Deoxyribonucleic Acid to High Specific Activity in vitro by Nick Translation with DNA Polymerase I*; J. Mol. Biol.; vol. 113; pp. 237–251; 1977.

Feinberg, Andrew P. and Vogelstein, Bert; *A Technique for Radiolabeling DNA Restriction Endonuclease Fragments to High Specific Activity*; Analytical Biochemistry; vol. 132; pp. 6–13; 1983.

Beaucage, S. L. and Caruthers, M. H.; *Deoxynucleoside Phosphoramidites—A New Class of Key Intermediates for Deoxypolynucleotide Synthesis*; Tetrahedron Letters, vol. 22; No. 20, pp. 1859–1892; 1981.

Chang, Lucy M. S. and Bollum, F. J.; *Deoxynucleotide–Polymerizing Enzymes of Calf Thymus Gland*; The Journal of Biological Chemistry; vol. 246, No. 4; pp. 909–916; Feb. 25, 1971.

English language (Derwent) abstract of WO 98/59040 (Dec. 30, 1998).

* cited by examiner

AUTOMATABLE RAPID TEST FOR DETECTION OF CANCER, BASED ON TELOMERASE (HTC) MRNA WITH SPECIFIC PRIMERS AND PROBES

The invention relates to an automatable rapid test for detection of cancer based on telomerase(hTC) mRNA, to suitable starter nucleotides and oligonucleotide probes for this test and to a corresponding detection method and a test kit.

The genetic material of eukaryotic cells is distributed on linear chromosomes. The ends of these hereditary units are termed telomers, derived from the Greek words telos (end) and meros (part or segment). Most telomers consist of repeats of short sequences which are mainly constructed from thymine and guanine (Zakian, 1995). The telomer sequences of related organisms are often similar and these sequences are even conserved between species which are more phyllogenetically remote. It is a remarkable fact that the telomers are constructed from the sequence TTAGGG in all the vertebrates which have so far been examined (Meyne et al., 1989).

The telomers exert a variety of important functions. They prevent the fusion of chromosomes (McClintock, 1941) and consequently the formation of dicentric hereditary units. Chromosomes of this nature, possessing two centromers, can lead to the development of cancer due to loss of heterozygosity or the duplication or loss of genes.

In addition, telomers serve the purpose of distinguishing intact hereditary units from damaged hereditary units. Thus, yeast cells ceased dividing when they harboured a chromosome which lacked a telomer (Sandell and Zakian, 1993).

Telomers carry out another important task in association with DNA replication in eukaryotic cells. In contrast to the circular genomes of prokaryotes, the linear chromosomes of eukaryotes cannot be completely replicated by the DNA polymerase complex. RNA primers are required for initiating DNA replication. After the RNA primers have been eliminated and the Okazaki fragments have been extended and then ligated, the newly synthesized DNA strand lacks the 5' end because the RNA primer at that point cannot be replaced by DNA. For this reason, without special protective mechanisms, the chromosomes would shrink with every cell division ("end-replication problem"; Harley et al., 1990). The non-coding telomer sequences probably represent a buffer zone for preventing the loss of genes (Sandell and Zakian, 1993).

Over and above this, the telomers also play an important role in regulating cell ageing (Olovnikov, 1973). Human somatic cells exhibit a limited capacity to replicate in culture; after a certain time they become senescent. In this condition, the cells no longer divide even after being stimulated with growth factors; however, they do not die but remain metabolically active (Goldstein, 1990). Various observations provide support for the hypothesis that a cell determines from the length of its telomers how often it can still divide (Allsopp et al., 1992).

In summary, the telomers consequently possess central functions in the ageing of cells and in the stabilization of the genetic material and prevention of cancer.

The Enzyme Telomerase Synthesizes the Telomers

As described above, organisms possessing linear chromosomes are only able to replicate their genome incompletely in the absence of special protective mechanisms. Most eukaryotes use a special enzyme, i.e. telomerase, to regenerate the telomer sequences. Telomerase is expressed constitutively in the single-cell organisms which have so far been examined. By contrast, in humans, telomerase activity was only detected in germ cells and tumour cells whereas neighbouring somatic tissue did not contain any telomerase (Kim et al., 1994).

Activation of the Telomerase in Human Tumours

In humans, it was originally only possible to demonstrate telomerase activity in germ line cells and not in normal somatic cells (Hastie et al., 1990; Kim et al., 1994). After a more sensitive detection method had been developed (Kim et al., 1994) a low level of telomerase activity was also detected in haematopoietic cells (Broccoli et al., 1995; Counter et al., 1995; Hiyama et al., 1995). However, these cells nevertheless exhibited a reduction in the telomers (Vaziri et al., 1994: Counter et al., 1995). It has still not been clarified whether the quantity of enzyme in these cells is insufficient to compensate for the telomer loss or whether the measured telomerase activity stems from a subpopulation, e.g. of incompletely differentiated $CD34^+38^+$ precursor cells (Hiyama et al., 1995). In order to clarify this point, it would be necessary to detect the telomerase activity which was present in a single cell.

Interestingly enough, however, significant telomerase activity has been detected in a large number of the tumour tissues which have been tested to date (1734/2031, 85%; Shay, 1997), whereas no activity has been found in normal somatic tissue (1/196, <1%, Shay, 1997). In addition, a variety of investigations demonstrated that the telomers continued to shrink in senescent cells which were transformed with viral oncoproteins and that it was only possible to find telomerase in the subpopulation which survived the growth crisis (Counter et al., 1992). The telomers were also stable in these immortalized cells (Counter et al., 1992). Similar findings derived from investigations in mice (Blasco et al., 1996) support the assumption that reactivation of the telomerase is a late event in tumour regenesis.

Details about telomerase and in particular the human catalytic telomerase subunit and its sequence are given in WO 98/14592 (Genon Corp.) and WO 98/59040 (Bayer AG).

Detection of Telomerase mRNA for Cancer Diagnosis

Based on these results, a "telomerase hypothesis" was developed which links the loss of telomer sequences and cell ageing to telomerase activity and the genesis of cancer. In long-lived species such as humans, the shrinking of the telomers can be regarded as a tumour suppression mechanism. Differentiated cells, which do not contain any telomerase, cease dividing when the telomers have reached a particular length. If such a cell mutates, a tumour can only develop from it if the cell is able to extend its telomers. Otherwise, the cell would continue to lose telomer sequences until its chromosomes became unstable and finally die. Reactivation of the telomerase is presumably the main mechanism which tumour cells deploy in order to stabilize their telomers.

It follows from these observations and ideas that it should be possible to diagnose tumours by elevated expression of telomerase. Since telomerase activity has been detected in virtually all the tumour tissues tested to date, it would be possible to use a genetic test for diagnosing all types of cancer. This genetic test is particularly suitable for monitoring the progress of cancerous diseases, but can also be used as a prognostic test or for the early diagnosis of certain cancerous diseases.

Gene probe diagnosis, in particular in combination with amplification techniques, is a rapid, specific and highly sensitive method which permits an early identification of specific genes, gene fragments or single mutations on the DNA/RNA level. The technique can be carried out directly in the material to be examined. It is based on the DNA/RNA hybridization technique. i.e. the specific in vitro binding of complementary single-strand nucleic acid with formation of Watson-Crick base pairs. The DNA/DNA or DNA/RNA double strands formed are also referred to as DNA hybrids. For the detection of the specific DNA or RNA by the hybridization reaction, complementary sequence-specific gene probes are used. These gene probes are short, chemically synthesized oligonucleotide probes having a length of 10–200 nucleotides.

Photochemically (N. Dattagupta, P. M. M. Rae, E. D. Huguenel, E. Carlson, A. Lyga, I. S. Shapiro, J. P. Albarella, Analytical Biochem. 177, 85, 1989) or enzymatically by nick translation (Rigby, P. W. J. et al., J. Mol. Biol. 113, 237, 1977) or by random primed techniques (Feinberg and Vogelstein, Anal. Biochem. 132, 6, 1983), the gene probes can be provided with radioactive or non-radioactive labels. Suitable for this purpose is labelling with $^{32}$P NTPs or non-radioactive labelling with digoxigenin-dUTP, biotin-dUTP or direct labelling with enzymes such as alkaline phosphatase or horseradish peroxidase.

For the specific hybridization between the nucleic acid to be detected and the specific gene probe, the nucleic acids are initially separated into single strands by denaturation (heat or alkali treatment) and then hybridized together very specifically under stringent conditions, which are achieved by temperature, ionic strength of the buffers and organic solvents. When the hybridization conditions are suitable, the gene probe binds only to complementary sequences of the DNA or RNA to be detected. This hybridization reaction can be carried out in various test formats, for example as solid phase hybridization on a support, such as, for example, nitrocellulose-coupled target DNA or gene probe or as liquid hybridization. The evaluation (read out) takes place via the labelling of the gene probe with a reporter molecule such as stated above or, as in the reversed-phase hybridization system described herein, via the target DNA which is labelled during the amplification with digoxigenin-dUTP, and the gene probe which is labelled with fluorescein for the binding to magnetic particles. The hybridization complex composed of target DNA and labelled gene probe is quantitatively determined, after removal of unbound gene probe, via the reporter molecule used. This read out can take place directly in the case of fluorescent labelling or radiolabelling or indirectly by enzyme assays and immunological methods with antibody conjugates which comprise enzymes such as alkaline phosphatase and then make a colour reaction or chemiluminescence reaction possible.

The test sensitivity with gene probe diagnosis is in the range from $10^5$ to $10^6$ copies on the basis of detection of single genes. The test sensitivity can be increased by combination with DNA or RNA amplification techniques such as PCR (EP 200362), LCR (EP 320308), NASBA (EP 329822), Qβ (PCT 87/06270) or HAS technique (EP 427074). It is possible with these techniques to achieve up to $10^9$-fold multiplication of the DNA to be detected. The combination of amplification and hybridization thus makes it possible to detect single DNA molecules.

The invention furthermore relates to primers and probes for amplifying and detecting the mRNA of the human catalytically active telomerase subunit (hTC). The human catalytic telomerase subunit (hTC) is described in WO 98/59040, which is expressly incorporated herein by way of reference.

Oligonucleotides in purified form having a sequence which is identical or exactly complementary to an uninterrupted sequence, of a length of 10 to 500 nucleotides, of the mRNA of hTC.

Such an oligonucleotide may, in particular, be an oligodeoxyribonucleotide or an oligoribonucleotide or a peptide nucleotide acid (PNA).

Preference is given to oligonucleotides which specifically hybridize with the hTC mRNA of the telomerase from the T-motif region. 5' region and 3' region.

A DNA sequence or a degenerated variation of this sequence which codes for the protein hTC or a fragment of this protein or a DNA sequence which hybridizes with the DNA sequence under standard hybridization conditions.

A recombinant polynucleotide probe which comprises a DNA sequence or a degenerated variation of this sequence which hybridizes with hTC or a fragment of hTC.

The invention furthermore relates to a method for detecting a neoplastic disease in a patient, in particular to a method for identifying the presence of the hTC protein in a cell or a cellular sample, which method is based on the amplification of an hTC polynucleotide or hybridization of an hTC polynucleotide, primers or an hTC-complementary sequence with an hTC polynucleotide. In this case, the method comprises the following steps:

A. detection of the hTC mRNA in cellular samples in order to obtain a diagnostic value;

B. comparison of the diagnostic value with standard values for hTC mRNA in non-neoplastic ells of the same type as the test sample;

C. diagnostic values which are considerably higher than the standard comparative values indicate a neoplastic state.

The invention furthermore relates to a test kit for detecting hTC mRNA in cellular samples and bodily fluids, based on the above test principle. The test kit is preferably used for diagnosing cancerous diseases.

The test kit comprises in particular:

A composition consisting of a pair of human hTC polynucleotide PCR primers, the primers preferably consisting of sequences which correspond to the sequence of human hTC mRNA or are complementary to this sequence, and/or a composition which comprises a polynucleotide hybridization probe for the human hTC gene, the probe comprising 20–36, for example 30, successive nucleotides which correspond to the sequence of human hTC mRNA or are complementary to this sequence.

In the case of oligo- or polynucleic acids, functional equivalents are to be understood as meaning those compounds which differ in the nucleotide sequence but encode the same protein. This is the result, for example, of the degenerated genetic code.

The invention relates in particular to starter oligonucleotides comprising a nucleotide sequence selected from the group consisting of SEQ ID No. 1, SEQ ID No. 2, SEQ ID No. 4, SEQ ID No. 5, SEQ ID No. 7, SEQ ID No. 8, SEQ ID No. 9 and SEQ ID No. 10.

The starter oligonucleotides are preferably employed in suitable pairs, i.e, in the following sets:

A set of a starter oligonucleotide comprising the nucleotide sequence according to SEQ ID No. 1 and a starter oligonucleotide comprising the nucleotide sequence according to SEQ ID No. 2.

A set of a starter oligonucleotide comprising the nucleotide sequence according to SEQ ID No. 4 and a starter oligonucleotide comprising the nucleotide sequence according to SEQ ID No. 5.

A set of a starter oligonucleotide comprising the nucleotide sequence according to SEQ ID No. 7 and a starter oligonucleotide comprising the nucleotide sequence according to SEQ ID No. 8.

A set of a starter oligonucleotide comprising the nucleotide sequence according to SEQ ID No. 9 and a starter oligonucleotide comprising the nucleotide sequence according to SEQ ID No. 10.

The invention furthermore relates to optionally labelled oligonucleotide probes comprising a nucleotide sequence selected from the group consisting of SEQ ID No. 3. SEQ ID No. 6 and SEQ ID No. 11.

The invention furthermore relates to a method for detecting increased telomerase activity, characterized in that
   a) in a sample telomerase(hTC) mRNA is amplified using one or more starter oligonucleotides according to claim 1 and
   b) the amplification results are evaluated.

The invention furthermore relates to a test kit for detecting increased telomerase activity which contains one or more of the starter oligonucleotides.

The present invention describes an automatable genetic test for detecting cancerous diseases based on hTC-specific mRNA. The in situ tests based on the RNA component of telomerase which have hitherto been described had the disadvantage that a tumour-specific relevance was not noticeable. TRAP tests (Kim et al., Science, 266, 2011–2015, 1994) did show that the telomerase activity in various malignant tumours was increased. However, test specificity and sensitivity in this test have hitherto been unsatisfactory and not relevant for prognostic or diagnostic use (for example bladder carcinoma).

The present invention has the advantage that, by using special specific primers optimized with respect to length and sequence and a fully automated read out, it is possible to measure the amount of the telomerase amplicon formed directly via a chemiluminescence test or colorimetric test, the amplicon serving as a direct measure for the telomerase expression or telomerase activity. Since hTC telomerase is apparently the rate-limiting step in the catalytic activity of telomerase, this test provides a direct correlation between tumour tissue and telomerase activity on the nucleic acid level. Thus, in various tumours in stomach, intestine, lung, breast, ovary, prostate and in melanoma and osteosarcoma, strongly elevated telomerase values could be demonstrated; in contrast, in normal tissue such as lung, brain, kidney, intestine and blood, only few signals were found.

By using an RNA detector probe in combination with a DNA/RNA antibody, it was furthermore possible to increase the signal strength of the amplicon by a factor of 10 and the sensitivity of the test compared to customary DNA tests by a factor of 10–100. Because of this, it was possible to strongly reduce the amount of test material required and to improve the reliability of the test result considerably even when only little material for testing was available, owing to the considerably stronger signals. Automization of the process, which has already been developed, allows the read out of a large number of samples (>100) within 20 minutes.

The present invention describes specific primers and oligonucleotide probes and their use for the rapid detection of telomerase expression based on hTC mRNA. Read out with magnetic beads according to the methods described in Examples 5 and 6 allows the test to be carried out automatically, for example on the Immuno I, Bayer Diagnostics, Tarrytown. Using the primers and probes described, the test can also be carried out in a Taqman or Lightcycler.

In addition, this test is particularly suitable for the cellular analysis of any sample material (for example smears), even for in situ hybridization.

I. The primers were prepared by chemical synthesis from the gene sequence of the telomerase gene.
   The invention relates to primers and probes having a length of 15 to 40 (for example 15 to 30) nucleotides from the T-motif region, 5' region upstream of the start codon and the 3' region of a splice variant, according to sequences 1–11 listed in the sequence protocol.
   The preferred primers were chosen from the region
      a) which is specific for the telomerase F motif (primer 1+2 SEQ ID No. 1+2)
      b) which is specific for the 5' region (promoter region) (primer 4+5 SEQ ID No. 4+5)
      c) which is specific for the 3' splice region with splice variants (primer 7+8 SEQ ID No. 7+8 or 9+10).

II. The oligonucleotide probes were prepared by chemical synthesis.

III. The mRNA was isolated from clinical samples by special RNA isolation methods.

IV. Amplification of parts of the hTC mRNA was carried out using the specific primers from the T motif region, promoter region or splice variant region.

V. For detecting the amplicons, a capture probe is used which hybridizes with the amplified nucleotide region.

VI. The amplification was carried out with the aid of known amplification techniques, preferably the RT-PCR amplification method (U.S. Pat. No. 5,322,770).

VII. The specific amplification product was detected
   a) by direct electrophoresis of the amplification product in an agarose gel and staining by intercalating agents such as ethidium bromide
   b) by determining the fluorescence of tile amplification product which has been labelled during the amplification with fluorescent nucleotides or fluorescence-labelled primers. The amplification product is separated via additionally incorporated biotin (primer or nucleotide)
   c) and preferably by hybridization of the amplification product, which has been labelled during the amplification (for example digoxigenin d-UTP) with the above-mentioned fluorescein-labelled oligonucleotide probes. The hybridization complex is separated using fluorescein antibody-coated magnetic particles.
   d) Evaluation of the formed hybridization complex as a measure of the telomerase expression and thus telomerase activity is carried out using a chemiluminescence test with antidigoxigenin antibodies which are coupled to alkaline phosphatase and react with the digoxigenin incorporated into the amplicon.

The test is carried out in each case with a mixture of test tissue mRNA and a mixture of normal control tissue mRNA. In the case of normal telomerase gene expression, amplification with the specific primers gives only little amplicon and accordingly only a small chemiluminescence signal. In the case of neoplastic tissue, large quantities of amplicon are formed, giving a strong chemiluminescence signal.

The great advantage of this test is that, after amplification, it can be decided directly whether there is an increased concentration of telomerase mRNA, the test is automatable and, because there is only a single amplification step, is very fast and can be carried out in a less laborious and costly manner.

Selection and Synthesis of Primers

Specific primer sets for the amplification products were selected from regions of the telomerase gene which are specific for the hTC telomerase gene and have no homology with other RT motifs or other RT sequences. Primers having the sequence SEQ ID Nos. 1, 2, 4, 5, 7, 8, 9, 10 were synthesized, which give specific amplification products. Suitable primers preferably have a length of from 15 to 25 base pairs, particularly preferably from 17 to 22 base pairs.

The selected primers were chemically synthesized b the phosphoramidite method of S. L. Beaucage and M. Caruthers. Tetrahedron Letters. 22, 1859, 1981.

Selection and Synthesis of the Oligonucleotide Probes

The oligonucleotide probes specific for the amplification products of the primer sets were selected from regions of the telomerase gene which are specific for the hTC telomerase gene and have no homology with other RT motifs or other RT sequences and do not undergo hybridization with other RT motifs or other RT sequences. 30–36mers having the sequences SEQ ID Nos. 3, 6, 11 which are specific for the amplification products were synthesized.

Suitable probes preferably have a length of from 20 to 36 base pairs, particularly preferably from 25 to 36 and very particularly preferably from 30 to 36 base pairs.

Suitable probes may also have a length of from 25 to 30 base pairs.

The chemical synthesis took place by the phosphoramidite method of S. L. Beaucage and M. Caruthers, Tetrahedron Letters, 22, 1859, 1981.

Amplification of mRNA from hTC Telomerase

For amplification of the mRNA sequence of human telomerase, the abovementioned primers were in each case employed as primer sets (primers 1+2), (primers 4+5) or (primers 7+8, 9+10) for specific RT amplification of human telomerase mRNA. They yield a visible amplification product with the mRNA of neoplastic cells in an agarose gel.

In the RTPCR amplification it is possible to incorporate not only the 4 dNTPs (deoxyadenosine triphosphate, deoxyguanosine triphosphate, deoxycytidine triphosphate and thymidine triphosphate) but also, for example, digoxigenin-dUTP into the amplification product. This makes it possible to evaluate the amplification product with an antidigoxigenin antibody which comprises, for example, coupled alkaline phosphatase via a chemiluminescence test with AMPPD as substrate or a dye test with pNPP.

An alternative possibility is to incorporate fluorescence-labelled nucleoside triphosphates such as, for example, fluorescein-dUTP or coumarin-dUTPs into the amplification product and to identify the amplification product with much greater sensitivity than with ethidium bromide staining. On use of biotinylated primers it is thus possible for the fluorescence-labelled, biotinylated amplification product to be removed via streptavidin-coated magnetic particles and to be determined quantitatively in the fluorescence photometer. Preferably in this invention, a DNA capture probe and a digoxigenin-labelled amplification product are used. It is also possible to use a probe in the form of a fluorescein-labelled RNA probe which serves as capture probe and detector probe. The sensitivities achieved with this genetic test using a DNA/RNA antibody are distinctly better than with genetic tests customary to date for other targets, and thus very little starting material is required for carrying out the test.

Detection of the Telomerase Expression

The telomerase expression level can be determined using any analytical methods by the primer sets described in the invention directly after amplification of a part of the htC mRNA.

One possible read out method is staining of the amplification product, which has been separated by agarose gel electrophoresis, with intercalating agents such as ethidium bromide.

Another possibility is to incorporate fluorescence-labelled nucleoside triphosphates into the amplification product. This achieves a distinct improvement in the test sensitivity.

A further possibility is to use fluorescence-labelled primers for the amplification or to combine biotinylated primers with fluorescent nucleotides so that a terminally biotinylated, fluorescence-labelled amplification product results and can be bound to streptavidin-coupled magnetic particles and separated, and the fluorescence can be determined semiquantitatively.

The most sensitive and the preferred method is the described method of hybridization of the amplification products with the described oligonucleotide probe. On incorporation of, for example, digoxigenin-dUTP during the amplification and use of a biotinylated or fluorescenated oligonucleotide probe it is possible for the hybridization complex to be separated on streptavidin/fluorescein antibody-coated magnetic particles and, on use of antidigoxigenin-antibodies which are coupled to alkaline phosphatase, be evaluated semiquantitatively via chemiluminescence with AMPPD or CSPD as substrate. An alternative method is the amplification without any incorporation of marker molecules and detection of the amplicon by hybridization with a fluorescein-labelled capture probe and an additional RNA probe as detector probe or with a single fluorescein-labelled RNA capture and detector probe. Detection of the hybridized amplicon takes place in this case with a DNA/RNA antibody. This read out yields a high sensitivity and was developed specifically for the automated method in the Immuno I automate and successor instruments.

EXAMPLE 1

Synthesis of Starter Oligonucleotides (Primers)

The selected starter oligonucleotides (primers) were chemically synthesized by the phosphoramidite method of S. L. Beaucage and M. Caruthers. Tetrahedron Letters, 22, 1859, 1981. The following nucleotide sequences were synthesized:

| Detection of the telomerase motif: | |
|---|---|
| PCR primer 1: | SEQ ID No. 1 |
| PCR primer 2: | SEQ ID No. 2 |
| Detection of the 5' region: | |
| PCR primer 4 + 5: | SEQ ID No. 4 + 5 |
| Detection of the 3' region: | |
| PCR primer 7 + 8: | SEQ ID No. 7 + 8 |
| PCR primer 9 + 10: | SEQ ID No. 9 + 10. |

EXAMPLE 2

Synthesis and Selection of the Oligonucleotide Probes

The oligonucleotide probes were selected from the nucleotide region which contains the in each case amplified sequence of the different primer sets. Chemical synthesis of the selected oligonucleotide probes took place by the phosphoramidite method of S. L. Beaucage and M. Caruthers. Tetrahedron Letters. 2, 1859, 1981.

| T motif region: probe 3 | SEQ ID No. 3 |
|---|---|
| 5' region: probe 6 | SEQ ID No. 6 |
| 3' region: probe 11 | SEQ ID No. 11. |

The capture probe was labelled at the 3' end by the method of Bollum. The enzymes, Boyer ed., Vol. 10, p. 145, Academic Press, New York. The end-group labelling was carried out nonradioactively with fluorescein-dUTP (Chang L. M. S., Bollum T. J., J. Biol. Chem. 246, 909, 1971).

In a 50 ml mixture with 10 ml of reaction buffer (potassium cacodylate 1 mol/l; Tris/HCl 125 mmol/l; bovine serum albumin 1.25 mg/ml; pH 6.6: 25° C.) 1 to 2 mg of oligonucleotide. 25 units of terminal transferase, $CoCl_2$ 2.5 mmol/l and 1 ml of fluorescein-dUTP (1 mmol/l), about 50% 3' end labelling are achieved after 60 minutes at 37° C.

EXAMPLE 3
Telomerase-specific Amplification by the RT-PCR Method (Titan One Tube RT-PCR System)

The mRNA or total RNA was diluted and used in concentrations of 100 ng, 50 ng and 25 ng (10 µl). The samples were then initially charged and the prepared mixers were added (50 µl total volume/tube). To check for DNA contamination, the enzyme mix was replaced by Taq polymerase.

Mix 1
1 µl of PCR nucleotide mix (10 mM)
200 ng of forward primer (0.4–1 µm)
200 ng of reverse primer (0.4–1 µm)
2.5 µl of 100 mM DTT
0.2 µl of RNAsine (20 units)
2 µl of $MgCl_2$ (25 mM)
1.5 µl of Dig dUTP dil. 1:10 (25 nM)
doubly distilled water a.d. 15 µl Mix 2
10 µl of 5×RT-PCR buffer
1.5 µl of enzyme mix, doubly distilled water a.d. 25 µl
PCR tubes with dilutions of RNA (10 µl) are prepared. In each case 25 µl of mix 2+15 µl of mix 1 are added.
PCR profile for T motif:
20' 58° C./2' 94° C.//30" 94° C.__1' 54° C.__1' 68° C. 30 cycles
7' 68° C./4° C.
Boehringer: order No. 1855476

EXAMPLE 4
Direct Evaluation of the Amplification Product

For direct evaluation of the DNA amplification product, the intercalating agent ethidium bromide was employed after the amplification.

It is also possible to employ biotin-dUTP or digoxigenin-dUTP, and to carry out a dye read out with antibody-coupled alkaline phosphatase. It is also possible to use, with lower sensitivity, appropriately fluorescence-labelled primers.

The amplification product was loaded onto a 0.8% agarose gel and electrophoresed at 100 mA for 30 minutes. The fluorescence signals were evaluated directly under a UV transilluminator.

EXAMPLE 5
Gene Probe Test on RT Amplification Products

Combination of suitable target amplification methods such as the polymerase chain reaction (PCR) (EP 200362). LCR (EP 320308) and the gene probe technique achieves a significant increase in sensitivity compared with conventional gene probe read out methods.

The liquid hybridization tests were carried out with 100 ng of digoxigenated amplicon and fluorescenated capture probe according to Example 3 in a volume of 50 µl.

After heating at 100° C. for 10 minutes and subsequent cooling to 0° C., 50 µl of 2× hybridization mix (50 ml of 20SSC, 1 g of blocking reagent (Boehringer), 2 ml of 10% strength lauroylsarcosine, 200 ml of 20% strength SDS ad 100 ml doubly distilled $H_2O$) were added and hybridized at 37° C. for 5–10 minutes (oligonucleotide probe). The magnetic beads were pretreated with 1× hybridization mix and the liquid was, after separation using a magnet, pipetted off, the hybridization mixture and 100 µl of 1× hybridization mix were added, and the mixture was incubated agitating gently at room temperature for 5–10 minutes. The coupled hybridization complex was separated with the beads, the remaining liquid was pipetted off and the complex was washed once with buffer B (0.1 SSC: 0.1% SDS).

The blocking reaction and antibody reaction were subsequently carried out to detect the hybridization via chemiluminescence. The beads loaded with DNA were added 1× with 500 µl of buffer 2 (0.1 M maleic acid; 0.15 M NaCl pH 7.5; 1% blocking reagent (Boehringer)). Incubation at room temperature for 5 minutes was followed by separation, pipetting off and addition of 250 µl of antibody conjugate solution (ab 1:2 500 in buffer 2) and incubation at room temperature for 10 minutes, then separation, pipetting off and treatment with 500 µl of washing buffer 2×30 seconds, 1×2 minutes with gentle agitation. It was then incubated with detection solution with AMPPD 1:100 in buffer 3 at 37° C. for 10 minutes, and then the chemiluminescence was measured in a luminescence photometer at 477 nm (Lumacounter from Lumac).

EXAMPLE 6
Gene Probe Test on DNA Amplification Products with DNA/RNA Antibodies Read Out Combination of suitable target amplification methods such as the polymerase chain reaction (PCR) (EP 200362). LCR (EP 320308) and the gene probe technique achieves a significant increase in sensitivity compared with conventional gene probe read out methods.

The liquid hybridization tests were carried out with 100 ng of fluorescein-labelled RNA probe and amplified DNA according to Example 3 in a volume of 50 µl.

After heating at 100° C. for 10 minutes and subsequent cooling to 0° C., 50 µl of 2× hybridization mix (50 ml of 20×SSC, 11 g of blocking reagent (Boehringer), 2 ml of 10% strength lauroylsarcosine, 200 ml of 20% strength SDS ad 100 ml doubly distilled $H_2O$) were added and hybridized at 37° C. for 5–10 minutes (oligonucleotide probe). The magnetic beads were pretreated with 1× hybridization mix and the liquid was, after separation using a magnet, pipetted off, the hybridization mixture and 100 µl of 1× hybridization mix were added, and the mixture was incubated agitating gently at room temperature for 5–10 minutes. The coupled hybridization complex was separated with the beads, the remaining liquid was pipetted off and the complex was washed once with buffer B (0.1 SSC; 0.1%, SDS).

The blocking reaction and antibody reaction were subsequently carried out to detect the hybridization via chemiluminescence. The loaded beads were added 1× with 500 µl of buffer 2 (0.1 M maleic acid; 0.15 M NaCl pH 7.5: 1% blocking reagent (Boehringer)). Incubation at room temperature for 3 minutes was followed by separation, pipetting off and addition of 250 µl of antibody conjugate solution (ab 1:2 500 in buffer 2) and incubation at room temperature for 10 minutes, then separation, pipetting off and treatment with 500 µl of washing buffer 2×30 seconds, 1×2 minutes with gentle agitation. It was then incubated with detection solution with AMPPD 1:100 in buffer 3 at 37° C. for 10 minutes, and then the chemiluminescence was measured in a luminescence photometer at 477 nm (Lumacounter from Lumac).

EXAMPLE 7
mRNA Isolation Using the Oligotex Direct mRNA Micro Kit from Qiagen $2 \times 10^7$ cells (total) were centrifuged at 2,500 rpm for 5 min. The supernatant was decanted off and the pellet was dried from the top, resuspended in 800 μl of lysis buffer OL1 and incubated on ice for 3 min. In each case 400 μl of the pellet which has been lysed in OL1 were applied to 2 homogenization columns. The columns were then centrifuged at 13,000 rpm for 1 min and discarded. Following addition of 800 μl dilution butter ODB and mixing, the sample was centrifuged at 13,000 rpm for 5 min and the supernatant was then transferred into autoclaved 2 ml reaction vessels and 30–50 μl of Oligotex suspension were added (the suspension was pre-heated at up to 37° C. for 10 min and shaken and then stored on ice). The mixture was then shaken at RT for 10 min. After 5 minutes of centrifugation at 13,000 rpm, the supernatant was discarded and the pellet was resuspended in 350 μl of wash buffer OW1. The mixture was then centrifuged at 13,000 rpm for 5 min, the supernatant was discarded and the pellet was washed 2× with wash buffer OW2. After the second washing, the suspension was applied to the column and centrifuged. The reaction vessel was discarded and the column was placed onto a new reaction vessel which contained 2 μl of RNAsine. 125 μl of elution buffer OEB (70° C.) were applied to the column, mixed with the pellet and eluted at 13,000 rpm for 5 min. The two eluates were combined and the OD was measured at 260 nm.

EXAMPLE 8
Detection of the Telomerase mRNA in Clinical Sample Material (Normal/Neoplastic Tissue)

mRNA was isolated from the clinical sample material using the method described in Example 7. The RNA lysate was then amplified by means of suitable amplification methods as described in Example 5 with specific oligonucleotide primers. The amplified nucleic acid was then hybridized with the oligonucleotide probes described in the sequence protocol, and the specific hybridization complex formed under stringent conditions was separated using magnetic particles from Dynal and examined quantitatively by chemiluminescence read out as described in Example 6 or, preferably, Example 7.

The tumour material of various origin listed in Table 1 was used for isolating total RNA or m-RNA. Other positive controls used were cell cultures such as HeLa cells or Hek cells. Normal tissue from lung, brain, kidney, intestine and blood (leukocytes) served as negative controls. After processing of the RNA, an RT-PCR was carried out as end point PCR on a normal thermocycler or as kinetic PCR on the Lightcycler or the Perkin-Elmer Taqman.

The result is summarized in Table 1. Using the primer sets and probes of the novel telomerase assay, all tissue samples gave high signals comparable to the signals in the HeLa and Hek cells. In contrast, the normal tissue gave only very low background signals, even at the highest RNA concentration.

It was also possible to positively identify telomerase activity in the urine of patients having bladder carcinoma or in the sputum of patients having lung tumours. Thus, in addition to biopsy material, various bodily fluids, such as, for example, urine, sputum and blood, can be used as starting material for testing for elevated telomerase activity.

TABLE 1

Carcinoma and control tissue:

| Tumour | Name | Target | Result |
|---|---|---|---|
| Bladder | BXF 1218 5NS | mRNA | pos. |
|  | BXF 1258 7N3 | mRNA | pos. |
|  | BXF 1299 9N7 | mRNA | pos. |
|  | BXF 1301 14N9 | mRNA | pos. |
| Breast | MAXF 449/13N3 | mRNA | pos. |
| Bone | SXF 1410/8N2 | mRNA | pos. |
| Colon | CXF HAT 29 LX/5N3 | mRNA | pos. |
|  | CXF 158 18N4 | mRNA | pos. |
|  | CXF 280 11N2 | mRNA | pos. |
| Head/neck | HNXF 675/4N2 | mRNA | pos. |
| Lung | LXFS 538/13N8 | mRNA | Pos. |
|  | LXFS 650 9N2 | mRNA | pos. |
|  | LXFS 650 LX6 | mRNA | pos. |
|  | LXFL 529 6N3 | mRNA | pos. |
|  | LXFL 1072 7N3 | mRNA | pos. |
|  | LXFL 529 12N2 | mRNA | pos. |
|  | LXFA 526 12N9 | mRNA | pos. |
| Melanoma | MEXF 462/7N4 | mRNA | pos. |
|  | MEXF 514LX/2 | mRNA | pos. |
| Ovary | OVXF 899/33N8 | mRNA | pos. |
|  | OVXF 1023/33N8 | mRNA | pos. |
| Pancreas | PAXF 546 6N3 | mRNA | pos. |
|  | PAXF 736 9N6 | mRNA | pos. |
|  | PAXF 546 5N2 | mRNA | pos. |
|  | PAXF 736 6N3 | mRNA | pos. |
| Prostate | PRXF 1369/36 | mRNA | pos. |
| Controls: | | | |
| Cell lines | (positive controls) | | |
| HeLa mRNA and Hek 293 mRNA and total RNA | | | pos. |
| Normal tissue: | (negative controls) | | |
| Lung | total RNA/mRNA | | neg. |
| Brain | total RNA | | neg. |
| Kidney | total RNA | | neg. |
| Intestine | total RNA | | neg. |
| Blood | total RNA/mRNA | | neg. |

Amplification and detection took place via one- or two-step RT-PCR and chemiluminescence test, fluorescence or colorimetric read out, respectively.

```
Sequences:
Telomerase
T motif
Sequences from HTC.MPD 1 > 4014

Primer:

Telo Tmotif      SEQ ID No. 1    5'AgCgTgCgggACTgCgCT3'
Forward primer
(1592)
Telo T motif     SEQ ID No. 2    5'ACCCTCTTCAAgTgCTgT3'
Reverse primer
(1842)
```

-continued

Probe:

| Telo T motif Probe (1749-1712) Reverse sequence Telomerase 5' region Sequences from SAC85.MPD 1 > 8377 | SEQ ID No. 3 | 5'TCCgTgACATAAAAgAAAgACCTgAgCAgCTCgA3' |

Primer:

| For5050 | SEQ ID No. 4 | 5'TcgCggCgCgAgTTTCAggCA3' |
| Rev5180 | SEQ ID No. 5 | 5'TagTggCTgCgCAgCAgggA3' |

Probe:

| Probe5100 Telomerase 3' region | SEQ ID No. 6 | 5'AagCCCTggCACCggTCACCCCCgCgATgCCgCgCg3' |

Primer:

| Tfor1 Introl 14 Pos 1490 | SEQ ID No. 7 | 5'TgCCTgCTggTgTTAgTgTgT3' |
| Tfor2 Intron 14 Pos 1790 | SEQ ID No. 9 | 5'AAACCCAggCCAAgggCTTA3' |
| Trev1 Exon 16 Pos 2041 | SEQ ID No. 8 | 5'AgggTCTCCACAACACAgA3' |
| Trev2 Exon 16 Pos 2046 | SEQ ID No. 10 | 5'TTCTCAgggTCTCCACAACa3' |

Probe:

| T3'Probe Pos | SEQ ID No. 11 | 5'TCTCAggAgCAgAggCCgCgTATCACCACgACAgA3' |

What is claimed is:

1. Starter oligonucleotides comprising a nucleotide sequence selected from the group consisting of SEQ ID No. 1, SEQ ID No. 4, SEQ ID No. 7, SEQ ID No. 8, SEQ ID No. 9 and SEQ ID No. 10.

2. Set composed of a starter oligonucleotide comprising the nucleotide sequence shown in SEQ ID No. 1 and a starter oligonucleotide comprising the nucleotide sequence shown in SEQ ID No. 2.

3. Set composed of a starter oligonucleotide comprising the nucleotide sequence shown in SEQ ID No. 4 and a starter oligonucleotide comprising the nucleotide sequence shown in SEQ ID No. 5.

4. Set composed of a starter oligonucleotide comprising the nucleotide sequence shown in SEQ ID No. 7 and a starter oligonucleotide comprising the nucleotide sequence shown in SEQ ID No. 8.

5. Set composed of a starter oligonucleotide comprising the nucleotide sequence as shown in SEQ ID No. 9 and a starter oligonucleotide comprising SEQ ID No. 10.

6. Oligonucleotide probes, labelled where appropriate, comprising a nucleotide sequence selected from the group consisting of SEQ ID No. 3, SEQ ID No. 6 and SEQ ID No. 11.

7. Method for detecting increased telomerase activity, comprising:

a) amplifying hTC mRNA in a sample using one or more starter oligonucleotides according to claim 1;

b) detecting the amplicons produced in step a) by using a suitable oligonucleotide probe;

c) amplifying hTC mRNA in a control sample, using the same oligonucleotides used in step a), to form amplicons;

d) detecting the amplicons produced in step c) by using a suitable oligonucleotide probe;

e) evaluating the amplification results by comparing the amount of amplicons detected in step b) with the amount of amplicons detected in step d).

8. Method according to claim 7, wherein said suitable oligonucleotide probe, labelled where appropriate, comprises a nucleotide sequence selected from the group consisting of SEQ ID No. 3, SEQ ID No. 6 and SEQ ID No. 11.

9. Test kit for detecting increased telomerase activity comprising one or more of the starter oligonucleotides according to claim 1.

10. Test kit according to claim 9, which furthermore comprises one or more oligonucleotide probes, labelled where appropriate, comprising a nucleotide sequence selected from the group consisting of SEQ ID No. 3, SEQ ID No. 6 and SEQ ID No. 11.

* * * * *

UNITED STATES PATENT AND TRADEMARK OFFICE
CERTIFICATE OF CORRECTION

PATENT NO. : 6,808,883 B1
DATED : October 26, 2004
INVENTOR(S) : Wolfgang Springer et al.

It is certified that error appears in the above-identified patent and that said Letters Patent is hereby corrected as shown below:

Title page,
Item [56], References Cited, OTHER PUBLICATIONS, "Zakian, Virginia A,; *Telomeres: Beginning to Understand the End*; Sciencevol. 270; pp. 1601-1607; Dec. 8, 1995." should read -- Zakian, Virginia A,; *Telomeres: Beginning to Understand the End*; Science; vol. 270; pp. 1601-1607; Dec. 8, 1995. --.
"Sandell, Lisa L. and Zakian, Virginia A.; *Loss of a Yeast Telmere: Arrest, Recovery, and Chromosome Loss*; Cell, vol. 75; pp. 729-739; Nov. 19, 1993." should read -- Sandell, Lisa L. and Zakian, Virginia A.; *Loss of a Yeast Telomere: Arrest, Recovery, and Chromosome Loss*; Cell, vol. 75; pp. 729-739; Nov. 19, 1993. --.
"Beaucage, S.L. and Caruthers, M.H.; *Deoxynucleoside Phosphoramidites —A New Class of Key Intermediates for Deoxypolynucleotide Synthesis*; Tetrahedron Letters, vol. 22; No. 20, pp. 1859-1892; 1981." should read -- Beaucage, S.L. and Caruthers, M. H.; *Deoxynucleoside Phosphoramidites —A New Class of Key Intermediates for Deoxypolynucleotide Synthesis*; Tetrahedron Letters, vol. 22; No. 20, pp. 1859-1862; 1981. --.

Signed and Sealed this

Tenth Day of May, 2005

JON W. DUDAS
*Director of the United States Patent and Trademark Office*

SEQUENCE LISTING

<160> NUMBER OF SEQ ID NOS: 11

<210> SEQ ID NO 1
<211> LENGTH: 18
<212> TYPE: DNA
<213> ORGANISM: Homo sapiens

<400> SEQUENCE: 1
agcgtgcggg actgcgct                18

<210> SEQ ID NO 2
<211> LENGTH: 18
<212> TYPE: DNA
<213> ORGANISM: Homo sapiens

<400> SEQUENCE: 2
accctcttca agtgctgt                18

<210> SEQ ID NO 3
<211> LENGTH: 34
<212> TYPE: DNA
<213> ORGANISM: Homo sapiens

<400> SEQUENCE: 3
tccgtgacat aaagaaaga cctgagcagc tcga                34

<210> SEQ ID NO 4
<211> LENGTH: 21
<212> TYPE: DNA
<213> ORGANISM: Homo sapiens

<400> SEQUENCE: 4
tcgcggcgcg agtttcaggc a                21

```
<210> SEQ ID NO 5
<211> LENGTH: 20
<212> TYPE: DNA
<213> ORGANISM: Homo sapiens

<400> SEQUENCE: 5
tagtggctgc gcagcaggga                                              20

<210> SEQ ID NO 6
<211> LENGTH: 36
<212> TYPE: DNA
<213> ORGANISM: Homo sapiens

<400> SEQUENCE: 6
aagccctggc accggtcacc cccgcgatgc cgcgcg                            36

<210> SEQ ID NO 7
<211> LENGTH: 21
<212> TYPE: DNA
<213> ORGANISM: Homo sapiens

<400> SEQUENCE: 7
tgcctgctgg tgttagtgtg t                                            21

<210> SEQ ID NO 8
<211> LENGTH: 19
<212> TYPE: DNA
<213> ORGANISM: Homo sapiens

<400> SEQUENCE: 8
agggtctcca caacacaga                                               19

<210> SEQ ID NO 9
<211> LENGTH: 20
<212> TYPE: DNA
<213> ORGANISM: Homo sapiens

<400> SEQUENCE: 9
aaacccaggc caagggctta                                              20

<210> SEQ ID NO 10
<211> LENGTH: 20
<212> TYPE: DNA
<213> ORGANISM: Homo sapiens

<400> SEQUENCE: 10
ttctcagggt ctccacaaca                                              20

<210> SEQ ID NO 11
<211> LENGTH: 35
<212> TYPE: DNA
<213> ORGANISM: Homo sapiens

<400> SEQUENCE: 11
tctcaggagc agaggccgcg tatcaccacg acaga                             35
```